United States Patent [19]
Jacobs et al.

[11] Patent Number: 5,833,896
[45] Date of Patent: Nov. 10, 1998

[54] METHOD OF MAKING A HOLLOW FIBRE MEMBRANE

[75] Inventors: Edmund Petrus Jacobs; Ronald Douglas Sanderson, both of Stellenbosch, South Africa

[73] Assignee: Water Research Commission, South Africa

[21] Appl. No.: 659,744

[22] Filed: Jun. 6, 1996

[30] Foreign Application Priority Data

Jun. 6, 1995 [ZA] South Africa .......................... 95/4648

[51] Int. Cl.$^6$ .............................. D01D 5/24; D01D 5/247
[52] U.S. Cl. ..................... 264/41; 264/184; 264/209.1; 264/211.14; 264/211.17
[58] Field of Search ........................ 264/41, 184, 209.1, 264/211.14, 211.17

[56] References Cited

U.S. PATENT DOCUMENTS

| | | | |
|---|---|---|---|
| 3,975,478 | 8/1976 | Leonard | 264/41 |
| 4,181,694 | 1/1980 | Hashino et al. | 264/41 |
| 4,822,540 | 4/1989 | Manabe et al. | 264/41 |
| 4,830,796 | 5/1989 | Pittalis et al. | 264/41 |
| 4,906,375 | 3/1990 | Heilmann | 210/500.23 |
| 5,071,917 | 12/1991 | Pederson et al. | 525/241 |
| 5,096,640 | 3/1992 | Brody et al. | 264/49 |
| 5,151,227 | 9/1992 | Nguyen et al. | 264/41 |
| 5,181,940 | 1/1993 | Bikson et al. | 95/47 |

FOREIGN PATENT DOCUMENTS

| | | |
|---|---|---|
| 0362588 | 4/1990 | European Pat. Off. . |
| 0418082 | 3/1991 | European Pat. Off. . |
| 0504686 | 9/1992 | European Pat. Off. . |
| 0260868 | 10/1988 | Germany . |

OTHER PUBLICATIONS

Journal of Membrane Science, vol. 98, No. 3, 31 Jan. 1995, Amsterdam, NL, pp. 191–200, M.J. Han et al: "Changes in morphology and transport characteristics of polysulfone membranes prepared by different demixing condition".

Myeong–Jin Han et al. "Changes in morphology and transport characteristics of polysulfone membranes prepared by different demixing conditions" Journal of Membrane Science 98 (1995) pp. 191–200.

*Primary Examiner*—Leo B. Tentoni
*Attorney, Agent, or Firm*—James Remenick; Baker & Botts, LLP

[57] ABSTRACT

A method of making a hollow fiber membrane comprises extruding a membrane-forming polymer solution through the annulus of a tube-in-orifice spinneret (12) to form a nascent hollow membrane (32), there being a lumen coagulant in the lumen of the nascent membrane, and the outside of the nascent membrane being contacted with an external coagulant (34). The external coagulant has a solvent content which is such that, at the interface between the nascent membrane and the external coagulant, liquid—liquid phase separation rather than gelation is thermodynamically the favored process, and the membrane is then subjected to a vapor-phase non-solvent environment to induce precipitation of the phase-separated polymer.

13 Claims, 8 Drawing Sheets

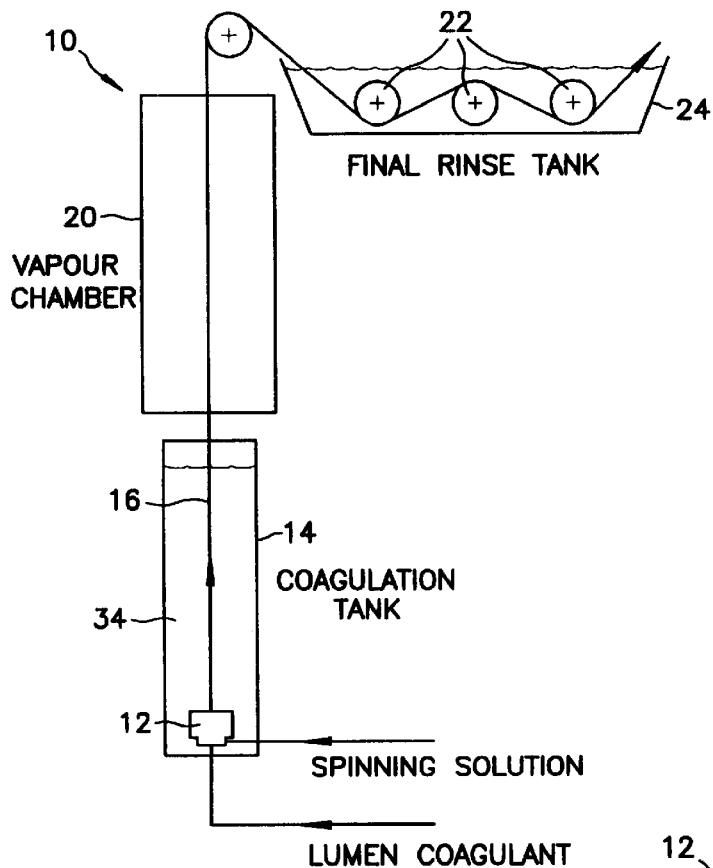
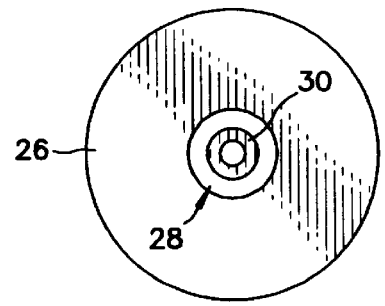
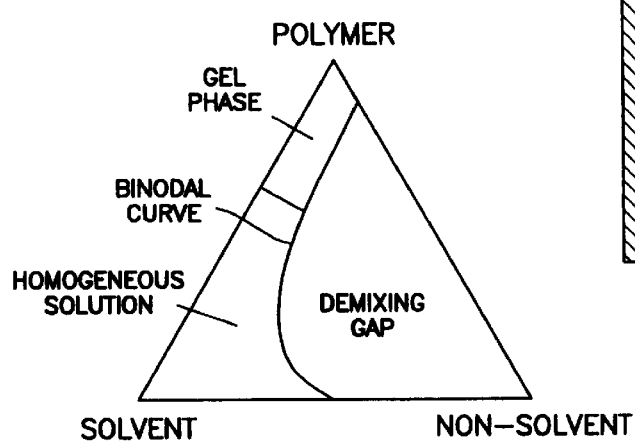
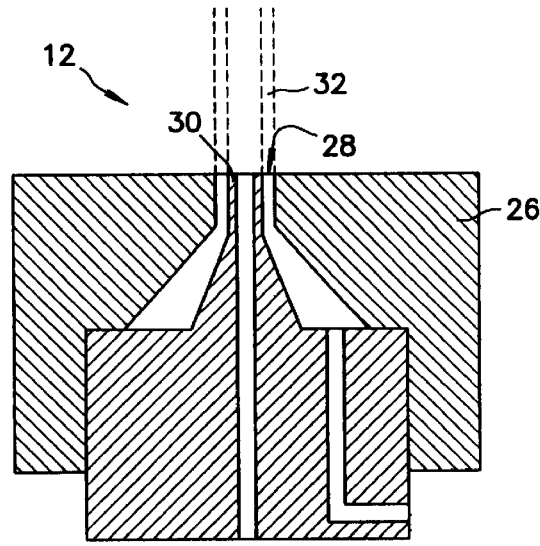

METHOD OF MAKING A HOLLOW FIBRE MEMBRANE

BACKGROUND TO THE INVENTION

THIS INVENTION relates to a method of making a hollow fibre membrane, particularly for use in membrane separation processes and membrane bioreactor applications.

SUMMARY OF THE INVENTION

According to the invention there is provided a method of making a hollow fibre membrane in which a membrane-forming polymer solution is extruded through the annulus of a tube-in-orifice spinneret to form a nascent hollow membrane, there being a lumen coagulant in the lumen of the nascent membrane, and the outside of the nascent membrane being contacted with an external coagulant, wherein the external coagulant has a solvent content which is such that, at the interface between the nascent membrane and the external coagulant, liquid—liquid phase separation rather than gelation is thermodynamically the favoured process, and wherein the membrane is then subjected to a vapour-phase non-solvent environment to induce precipitation of the phase-separated polymer.

The external coagulant may have a solvent content which is such that, in a phase diagram of the ternary system consisting of the solvent component of the coagulant, the non-solvent component of the coagulant, and the polymer, and having a solvent-non-solvent axis, a demixing gap, and a binodal curve at the boundary of the demixing gap, the composition of the external coagulant lies within 5% of the point where the binodal curve intersects the solvent-non-solvent axis.

In another aspect of the invention the external coagulant may have a solvent content which is such that, in a phase diagram of the ternary system consisting of the solvent component of the coagulant, the non-solvent component of the coagulant, and the polymer, and having a solvent-non-solvent axis, a demixing gap, and a binodal curve at the boundary of the demixing gap, the composition of the external coagulant lies outside the demixing gap.

The external coagulant may be a solution of polymer solvent in water.

The water content of the external coagulant may be less than 20% by volume, and preferably less than 9% by volume. In particular, the water content of the external coagulant may be about 2% by volume.

The vapour of the non-solvent vapour phase environment may be water vapour.

The polymer of the membrane-forming polymer solution may be polysulphone or polyethersulphone.

The invention will now be described in more detail, by way of example, with reference to the accompanying drawings.

BRIEF DESCRIPTION OF THE DRAWINGS

In the drawings:

FIG. 1 diagrammatically illustrate apparatus for making a hollow fibre membrane in accordance with the invention;

FIG. 2 is a vertical section through a spinneret used in the apparatus;

FIG. 3 is a plan view of the spinneret;

FIG. 4 is a ternary phase diagram of the polymer solvent system;

DETAILED DESCRIPTION OF PREFERRED EMBODIMENTS

Figure 5:
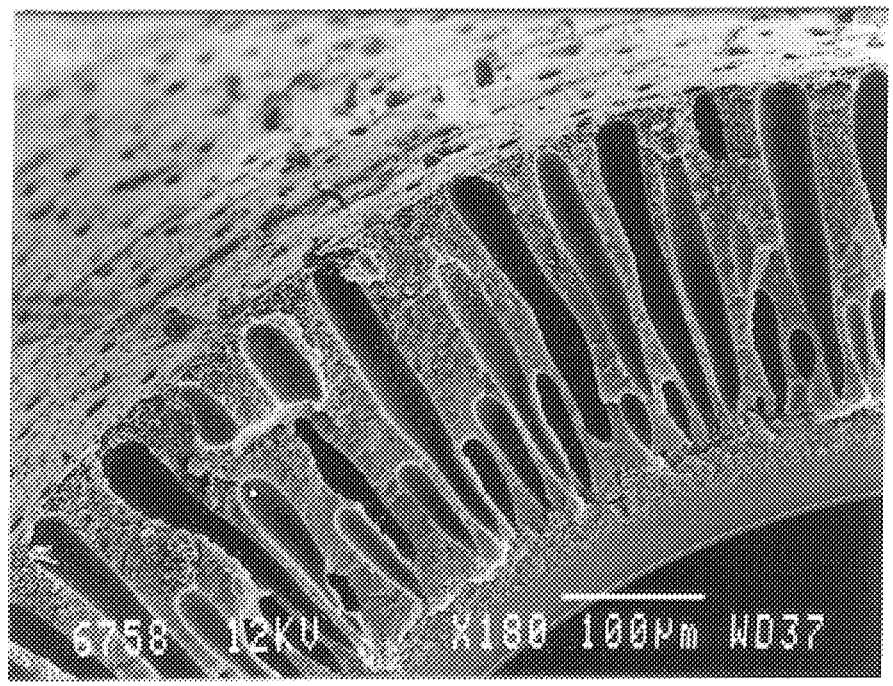
FIG. 5 is an electron micrograph of a cross-section of membrane PSf-1.

The Tables referred to in the description appear at the end of the description.

Referring first to FIGS. 1 to 3, reference numeral 10 generally indicates apparatus for making a hollow fibre membrane, the apparatus comprising a spinneret 12 for extruding a spinning solution upwardly into a coagulation tank 14 to form a hollow fibre membrane 16. The membrane 16 exits the coagulation tank 14 and then enters a high humidity vapour chamber 20. From the vapour chamber 20 it passes around a series of idler rollers 22 through a rinse tank 24.

The spinneret 12 is of conventional construction and comprises a body 26 which defines an orifice 28, and centrally of the orifice there is a tube 30. A membrane-forming polymer solution (also referred to herein as the spinning solution) is injected into a chamber formed around the tube 30. This causes a nascent membrane 32 to be extruded from the annulus between the body 26 and the tube 30. A lumen coagulant is injected into the nascent membrane via the tube 30.

In a preferred embodiment of the invention the spinning solution has the following composition:

1. Polymer resin in the form of polysulphone (PSf) or polyethersulphone (PES). The higher the concentration of the polymer resin, the higher the density of the skin structure of the resultant fibre membrane. The upper limit of the concentration is determined by porosity (or density) of the substructure or skin that is required. If the concentration of the polymer resin is too low, the fibre membrane loses its mechanical integrity. A concentration of between 18 and 29 m/m % has been found to give good results.

2. A polymer additive in the form of polyethylene glycol (PEG600), at a concentration of between 10 and 35 m/m %.
3. A true solvent in the form of N-methyl, 2-pyrrolidine (NMP). Alternatively other aprotic solvents such as N,N-dimethylacetamide (DMAc) of N,N-dimethylformamide may be used.
4. A non-solvent additive in the form of methyl Cellusolve (MC), at a concentration of between 0 and 20 m/m %.

A formulation that has been found to give good results consisted of PSf 22%, NMP 36%, MC 10%, and PEG600 32%.

The nascent membrane 32 with the non-solvent coagulant in the lumen thereof rises in a bath of external coagulant 34 in the coagulation tank 14.

The spinning solution is metered through the annulus of the spinneret at a rate of typically 4 m/min. The outside diameter of the annulus is typically 2,1 mm and the inside diameter typically 1,2 mm.

The lumen coagulant may be pure water or water containing fractions of solvent, or organic or inorganic additives, depending on the final internal skin morphology that is required.

The liquid 34 in the coagulation bath consists of water with a relatively high solvent content. The water content should be less than 20% by volume and is typically about 2% by volume. The liquid 34 should be at about room temperature, i.e. about 22° C. It has been found that when this is the case the gelation process by which an external skin is normally formed on the outside of the nascent membrane does not take place, as liquid—liquid phase separation is thermodynamically the favoured process.

Gelation does, however, take place on the inside of the membrane, due to the high non-solvent content of the lumen coagulant.

Nucleation and growth of respectively polymer-poor and polymer-rich phases follows and the macro- and micro-structure of the membrane is determined. The polymer in the outer regions of the membrane does not precipitate due to the high concentration of solvent in the coagulation tank 14. The coagulation tank 14 preferably has a height of about 1,2 m.

After leaving the coagulation tank 14, the membrane 18 passes through the vapour chamber 20 in which there is a highly humid atmosphere. The humidity in the chamber 20 should be sufficiently high to induce coagulation of the phase separated polymer, thereby creating a membrane with an open external surface structure. The chamber 20 has a height of between 300 and 1200 mm, typically 1000 mm. The relative humidity in the chamber is raised by cascading hot water (at a temperature of typically 40° C.) down the inside of the chamber.

From the chamber 20 the membrane 16 passes through the rinse tank 24 where solvent is extracted before further processing of the membrane takes place.

It is important for the membrane to be drawn from the spinneret 12 with as little tension as possible. Too much tension leads to the formation of micro-cracks in the internal skin layer, which in turn leads to leaking of the lumen coagulant and destruction of the external surface structure of the membrane.

Membranes with unique morphologies can be produced by manipulating and adjusting the various factors that control the wet-phase inversion manufacturing process by which most asymmetric membranes are formed. In this way it is possible to produce low-molecular-mass cut-off ultrafiltration or microfiltration membranes from the same polymer by changing only the polymer concentration and spinning solution solvent system used. Although the final membrane morphology is largely determined by the spinning solution formulation, the fabrication protocol plays an equally important role in controlling the properties and performance of the final membrane structure. By careful adjustment of the membrane spinning solution formulation and fabrication protocol, capillary ultrafiltration membranes were developed for use in a membrane bioreactor.

It is known that delayed precipitation leads to the formation of Type I membranes which nearly always exhibit sponge-like structures with dense skin layers. Conversely, instantaneous or rapid precipitation leads to the formation of Type II membranes which are often thin-skinned with finger-like macrovoids in the sub-layers. The following generalisations apply to the formulation of spinning solutions for the formation of Type II membrane:

strong non-solvents (e.g. water) increase the miscibility gap in the ternary phase diagram and favour composition profiles that support rapid phase separation;

low initial polymer concentration will favour the formation of membranes with thin open-porous skin layers and macrovoids;

small additions of non-solvent additive(s) to the spinning solution will favour the formation of thin-skinned membranes with macrovoids; and addition of high solvent concentrations to the coagulation medium will favour the formation of low-density and thinner skin layers, with sponge-like sub-layers.

Some experimental work that was done is described in what follows.

Approach

The method by which the membranes described were fabricated was based on known wet-phase inversion techniques. The following considerations were used to determine the formulation of the internal and external coagulants, and of the spinning solution.

Skin-formation, i.e. gelation, on the lumen side generally results from contact with a strong non-solvent. Pure water with no solvent or other additives was therefore used as the internal coagulant to generate a thin-skinned membrane.

The formation of macrovoids arises from the nucleation and rapid growth of polymer-poor nuclei. In the fabrication of conventional hollow fibre membranes, measures are often taken to suppress the formation of macrovoids. To achieve the objects of the present invention, however, the formation of solvent-rich nuclei had to be stimulated, and the solvent composition of the spinning solution and of the external coagulant chosen to sustain growth of the macrovoid from just below the skin layer all the way to the membrane exterior.

To form an open-pore surface on the outside of the membrane, gelation on contact with the external coagulant bath had to be suppressed. Gelation (skin-formation) can be suppressed and liquid—liquid phase separation thermodynamically favoured if the coagulant bath contains low concentrations of non-solvent. If the composition of the external coagulant bath reflects that of the polymer-poor phase front as it nears the membrane exterior, there should be no driving force for diffusion (i.e. no concentration gradient) and the phase-inversion process should therefore cease. As a first approach, a 20% aqueous solution of NMP was chosen as a starting point. As a second approach, the composition of the external coagulation bath was selected, instead, to have a solvent/non-solvent ratio close to the cloud-point of the spinning solution.

Membrane-formation

Capillary membranes are formed by extruding (spinning) a polymer solution through an annular tube-in-orifice spinneret, by means of a stainless steel precision-gear metering pump. Such a spinneret was positioned at the bottom of the non-solvent coagulation tank, and the membrane was drawn vertically from the spinneret at a rate of 4 m/min. Pure water was metered into the lumen of the membrane, so as to form a thin, dense inner skin layer. As the external coagulant was high in solvent content, and the membrane formation by phase-inversion was not completed where the nascent membrane left the coagulant bath, the nascent membrane was then exposed to a non-solvent vapour atmosphere. This completed the process of membrane-formation by phase-inversion, and the membrane could then be transferred to guide rollers in the rinse tanks without damage.

Grade 3010 Ultrason S (polysulphone) and Ultrason E (polyethersulphone) from BASF were used as the polymer, NMP as the solvent, and MC as the non-solvent in the spinning solution. The solvent and non-solvent(s) were vacuum distilled in an inert atmosphere and stored over a 3 Å molecular sieve. A chemically pure, low molecular mass (liquid) polymer additive in the form of PEG600, and an industrial grade, high molecular mass polymer additive in the form of polyvinylpyrrolidone K30 (PVP) were used.

Spinning Solution Preparation

The composition of some of the initial spinning solutions that were examined are given in Table 1. The solutions were prepared in 2 L resin kettles equipped with a high-speed overhead stirrer, and placed in an oil bath. The solvation temperature was maintained at 60° C. The shaft of the stirrer was passed through a Liebig condenser which prevented loss of low boiling point solvent(s). A minimum period of 48 h was required to obtain a homogeneous solution. The solution was then decanted into Schott bottles, rotated slowly for 48 h on rollers at ambient temperature, filtered through a 5 $\mu$m stainless-steel filter and degassed in a desiccator for 24 h, directly before use.

After fabrication, the membranes were rinsed in pure water for 24 h, and then conditioned in a 1:1 aqueous glycerine solution before they were dried out in a high-humidity chamber at ambient temperature for a period of 7 days. The membrane specimens did not undergo thermal or any other form of post-treatment.

Sample Preparation for SEM Analysis

Specimen membranes were fractured at liquid nitrogen temperatures and then sputter-coated with gold at low vacuum (<0,1 torr) in an argon atmosphere and 20 mA current, for a period of two minutes. The membrane specimens were observed with a Jeol JSM 840 scanning electron microscope (SEM).

Results and Discussion

Figure 6:
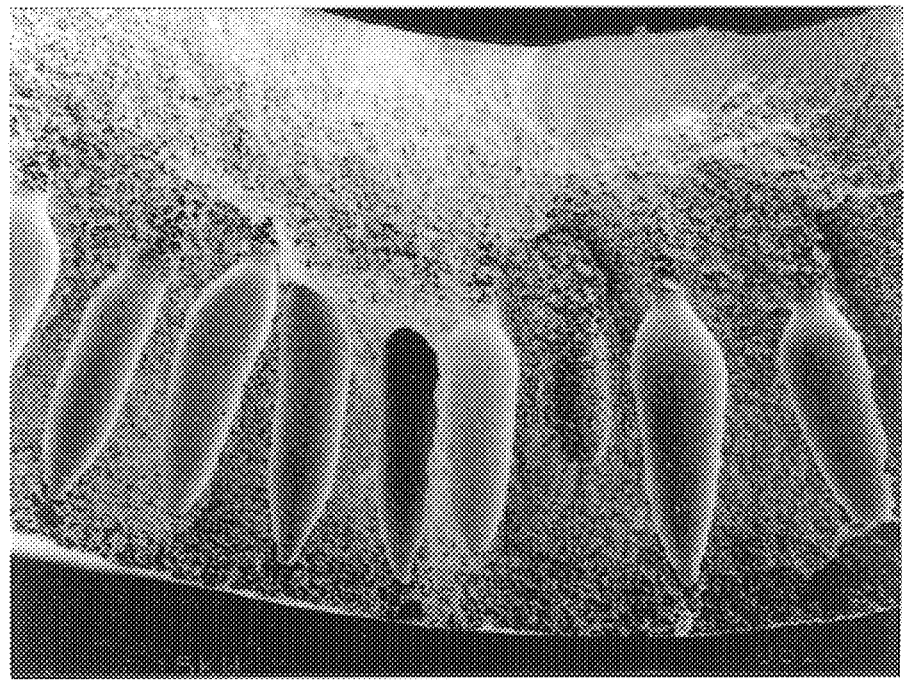
FIG. 6 is an electron micrograph of a cross-section of membrane PSf-2.
Figure 7:
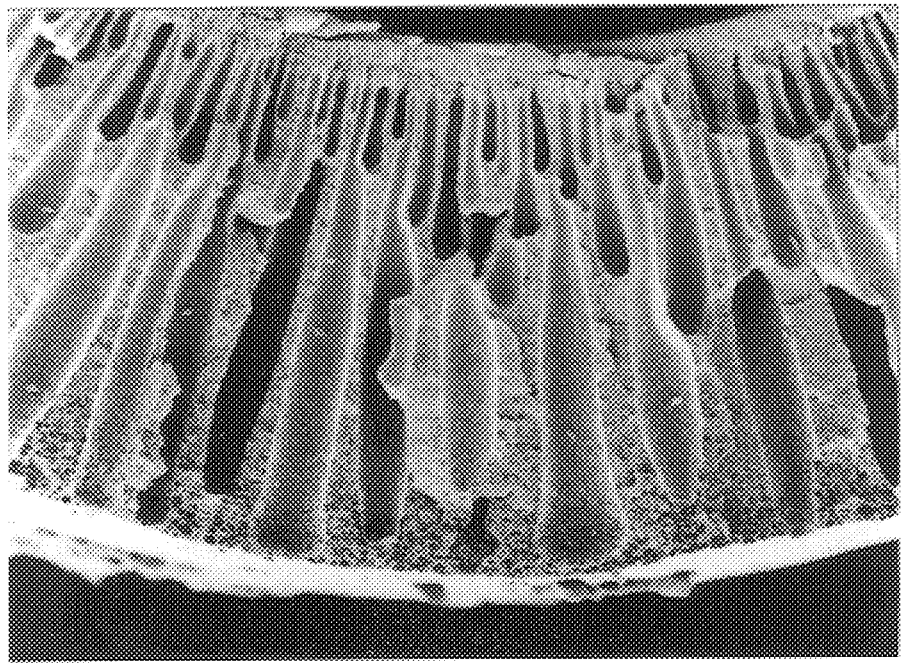
FIG. 7 is an electron micrograph of a cross-section of membrane PSf-3.
Figure 8:
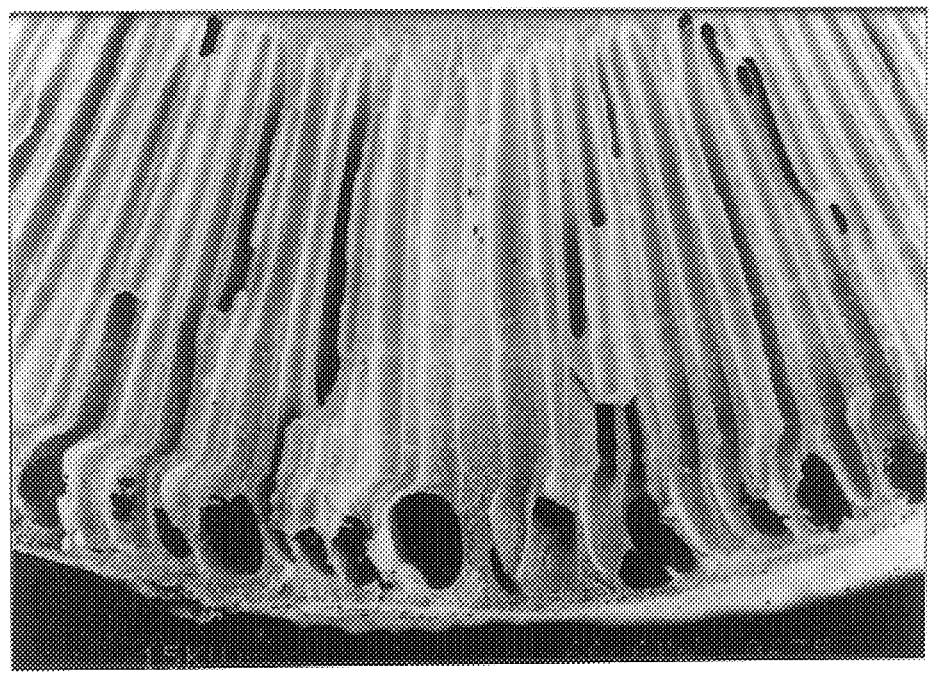
FIG. 8 is an electron micrograph of a cross-section of membrane PSf-4.

As a first approach the membranes were spun into an aqueous external coagulation bath with a solvent content of 80%, using the same solvent as that used in the spinning solution. FIG. 5 shows a micrograph of the cross-section of membrane PSf-1 (see Table 1). A large number of the macrovoids seen in FIG. 5 were dead-ended, that is, not extending the full width of the membrane wall. FIGS. 6, 7 and 8 are micrographs of cross-sections of membranes PSf-2, PSf-3 and PSf-4 (see Table 1). It is evident from these FIGS. 6, 7, and 8 that membrane PSf-4 showed some promise for further development as the macrovoids present in it were narrow and their spacing strikingly regular. The macrovoids of the membrane shown in FIG. 8 were also fully developed and open-ended, few appearing not to extend the full width of the membrane.

Although some of the features of membrane PSf-4 were what was required, the membrane shown in FIG. 8 still required further modification. It appeared from the micrograph of FIG. 8 that the wall on the lumen side of this membrane was skinned and not microporous. The spinning solution therefore had to be modified further to promote greater porosity, as this was through to be necessary for the membrane to be effective for use in a bioreactor. The formulation was adjusted by decreasing the polysulphone concentration and increasing the low molecular mass polymer additive concentration. The resultant formulation (PSf-5), which was subsequently used in all further experiments, is given in Table 2.

Figure 9:
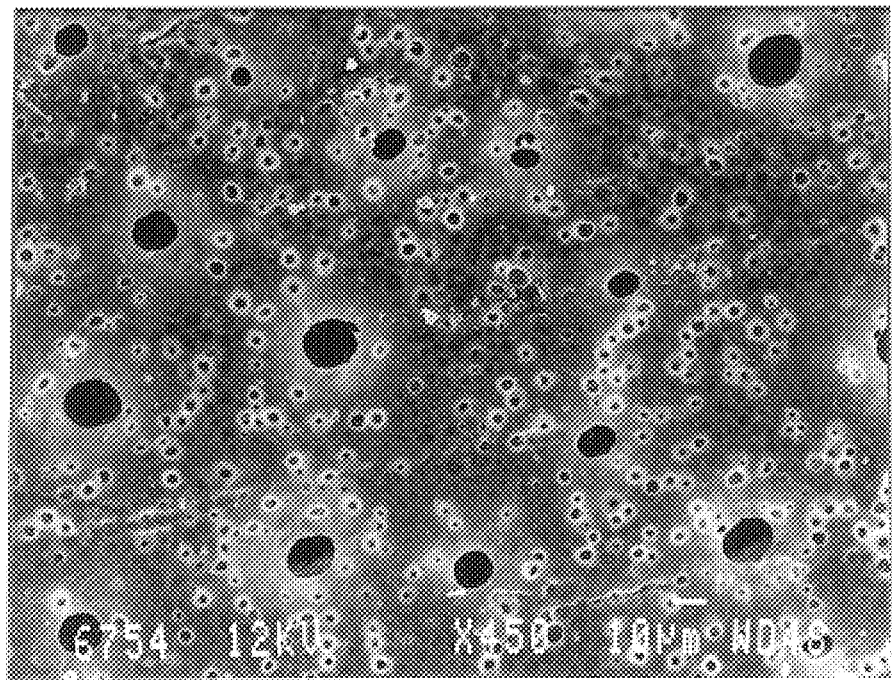
FIG. 9 is an electron micrograph showing the external skin-surface of a polysulphone membrane coagulated in a 20% aqueous solvent coagulant.

It proved difficult to prevent the formation of a skin layer on the outside of the membrane. In FIG. 5 an external skin layer is clearly visible in the micrograph, even through the external coagulant was high in solvent content and therefore had little precipitation potential. However, not all membranes which coagulated in the 20% aqueous solvent had well-defined external skin layers, as regularly spaced cavities were prominent in some of the membranes (see FIG. 9).

If earlier assumptions regarding skin-formation were correct, the aqueous contents of the external coagulant had to be reduced considerably, below the 20% level, to prevent gelation, nucleation or phase-separation by any of the various mechanisms that are responsible for this. However, the lower limit of the aqueous content of the external bath was that point at which the coagulant actually started to re-dissolve the nascent membrane. To determine this point, 50 g of membrane PSf-5 spinning solution (see Table 2) was shaken up with an equal amount of aqueous solvent mixture at 22° C. The spinning solution dissolved without any sign of cloudiness in aqueous mixtures containing up to 8% water, although dissolution of the spinning solution became progressively slower at higher water contents. The first sign of cloudiness appeared at water concentration levels of 9% and greater. It was therefore reasoned that a water concentration level of 9% should be regarded as the preferred upper aqueous limit of the external coagulant bath in the case of PSf membranes.

Figure 10:
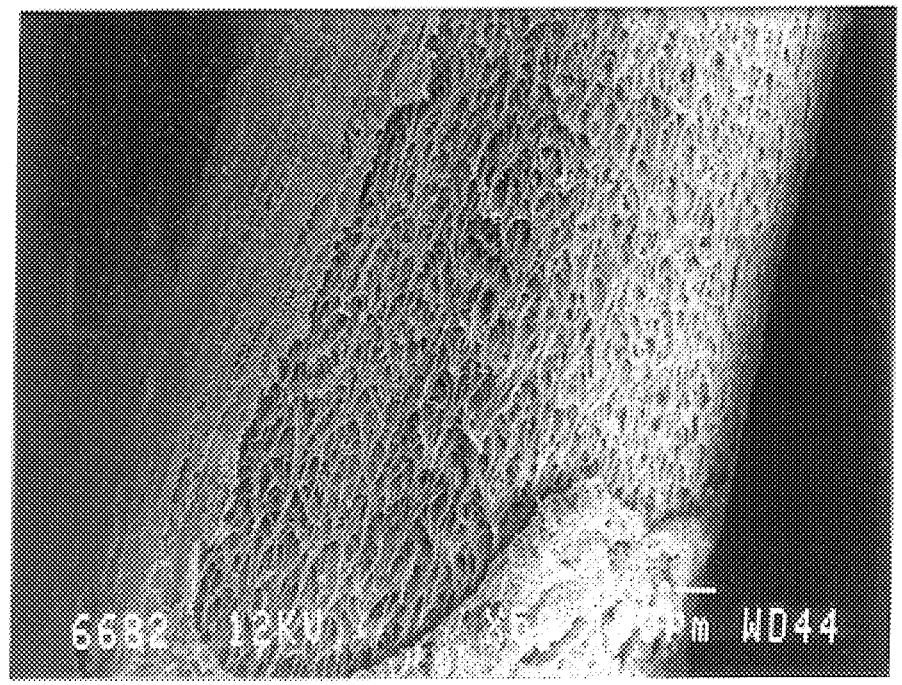
FIG. 10 is an electron micrograph showing the external surface of membrane PSf-5/1 cast into a 4,3% aqueous solvent coagulant.
Figure 11:
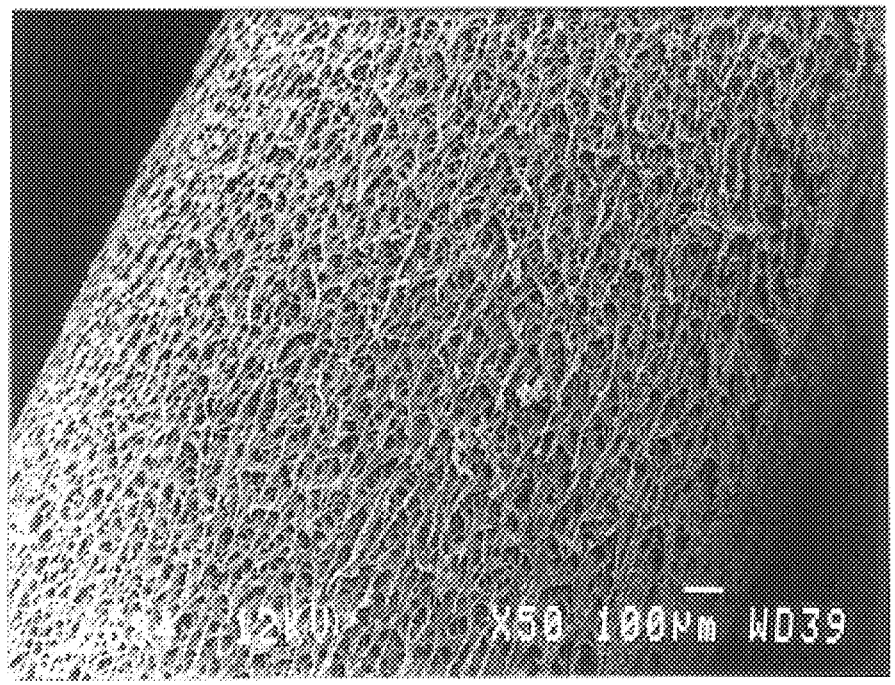
FIG. 11 is an electron micrograph showing the external surface of membrane PSf-5/2 cast into a 6,1% aqueous solvent coagulant.
Figure 12:
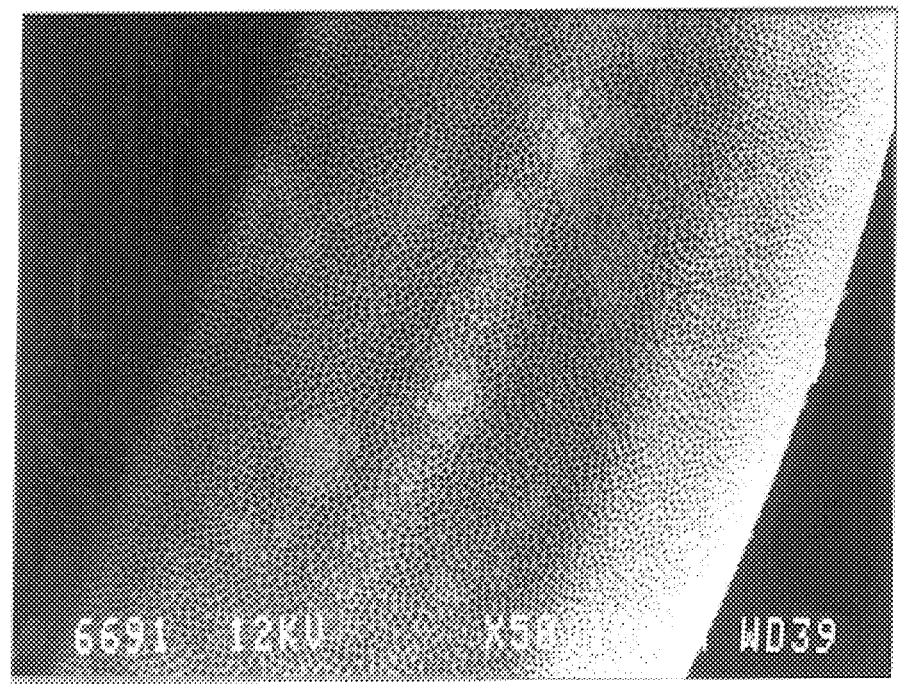
FIG. 12 is an electron micrograph showing the external surface of membrane PSf-5/3 cast into a 7,9% aqueous solvent coagulant.

The next step in the development of the bioreactor membrane was to spin the polysulphone membranes into external coagulants that contained less water than the proposed 9% upper limit. Table 3 shows the water content of three of the solvent coagulation baths that were used. The compositions of each of the three coagulation baths had a pronounced effect on the exterior morphology of the membrane. FIGS. 10, 11 and 12 show the external surface textures of the respective membranes, and give a clear indication of the pronounced effect of decreasing the water content. In external coagulants with a low aqueous content the outer regions of the membrane seemed to re-dissolve (and smudge), to form a secondary skin layer of low definition (see FIGS. 10 and 11). At higher water concentrations gelation occurred and skin morphologies similar to that shown in FIG. 9 again become prominent.

Figure 13:
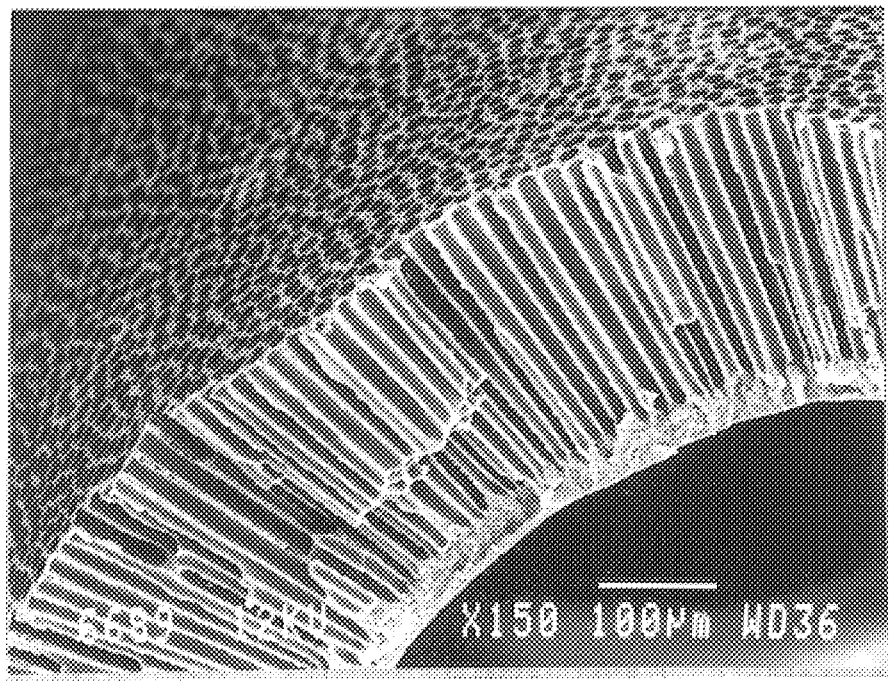
FIG. 13 is an electron micrograph showing a cross-section of membrane PSf-5/3.

FIG. 13 shows a cross-section of membrane PSf-5, which was cast into a 7,9% aqueous solvent coagulation bath. The ultrafiltration membrane had a well-defined internal skin layer and the spacing of the open-ended narrow-bore macrovoids which radiated from the internal skin layer was strikingly regular. It was clear from the micrograph that coagulation was initiated from the lumen side. Formation of solvent-rich nuclei below the skin layer was possibly enhanced by the controlled tension under which the membrane was drawn away from the spinneret.

Shrinkage (the outside diameter of the spinneret was 1,2 mm, whereas the final membrane diameter was 1,8 mm) may have played a role in sustaining the exchange of non-solvent and growth of the finger-like cavities across substantially the full width of the membrane. The composition of the external coagulant fell just outside the demixing gap on the ternary phase diagram (see FIG. 4) and did not affect the state of the nascent membrane with which it was in contact. It was found desirable for the solvent content of the external coagulant to be within 5% of the point where the binodal curve intersects the solvent-non-solvent axis. Surface tension within the polymer-rich phase maintained the structural integrity of the soft, viscous, coagulated, polymer-rich phase until it was finally set when brought into contact with the non-solvent vapour in the vapour chamber.

Figure 14:
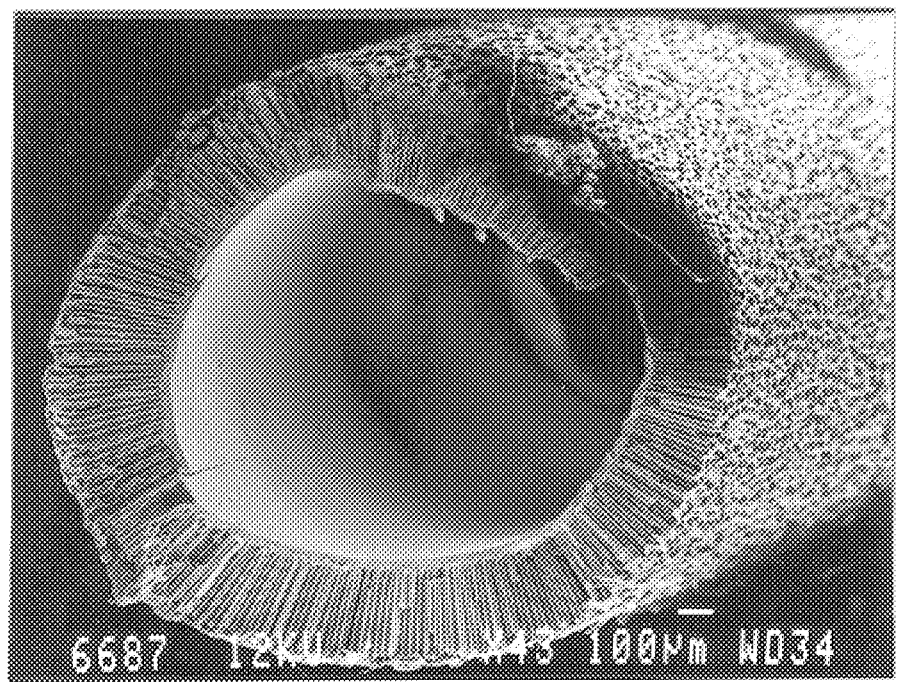
FIG. 14 is an electron micrograph showing the finger-like macrovoids of membrane PSf-5/3.
Figure 15:
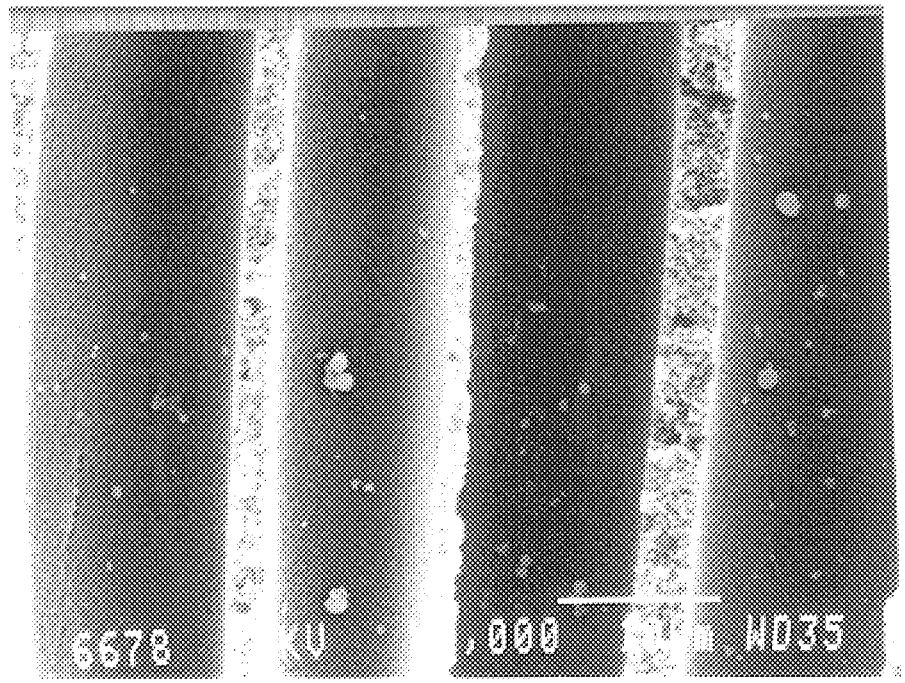
FIG. 15 is an electron micrograph showing a close-up of the macrovoids of membrane PSf-5/3, to reveal the macroporous morphology of the macrovoid walls.
Figure 16:
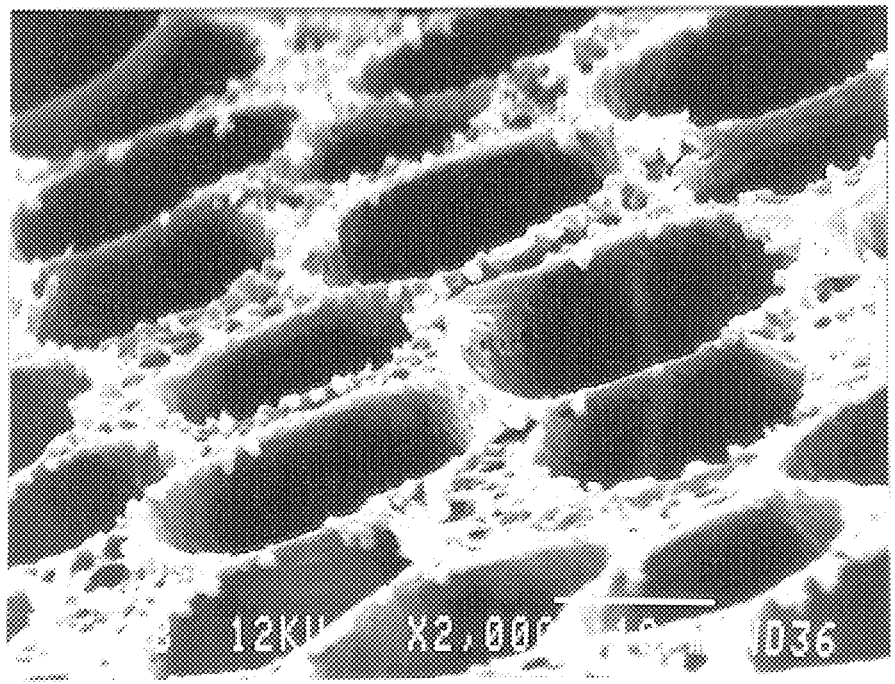
FIG. 16 is an electron micrograph showing a close-up of the exterior surface of membrane PS-5/3.

FIG. 14 again shows membrane PSf-5 and the striking uniformity of the macrocells which, as shown in FIG. 15, had highly porous walls. The average diameter of the macrovoids was 20 µm (see FIG. 16). From the micrographs the diameter of the membrane was calculated to be 1,8 mm and the diameter of the macrovoid openings 25 µm (i.e. the diameter of the macrovoids plus one times the thickness of the walls defining them). Based on these calculations, it was estimated that there were more than $9 \times 10^6$ macrovoids per meter-length of membrane.

It is commonly observed that the presence of macrovoids in the substructure of membranes does not always benefit the mechanical integrity of the membrane. In the present case it was important to reduce the thickness of the internal skin layer to stimulate macrovoid formation and maximize the void length. Because of the resultant reduction in support provided by the skin layer, the membrane resistance and hence the hydrostatic driving force that the membrane can sustain were also reduced. The membranes were nonetheless reasonably robust with instantaneous burst-pressures ranging from 2,3 MPa for membrane PSf-1 to 1,8 MPa for membrane PSf-5.

Figure 17:
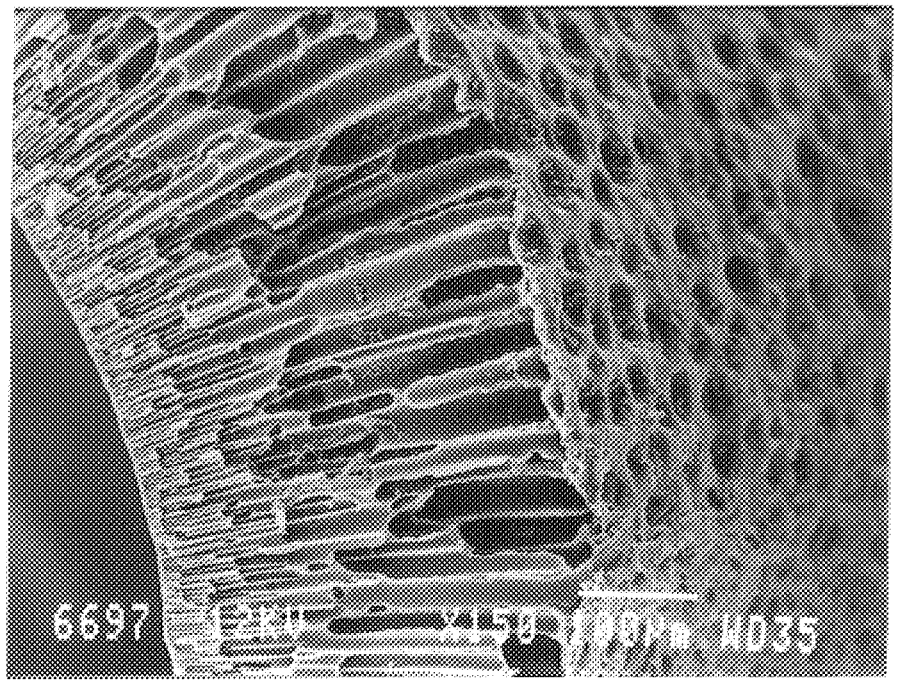
FIG. 17 is an electron micrograph showing a cross-section of polyethersulphone membrane PES-1.

Membranes were prepared from polyethersulphone by the same method, although with minor modifications to the fabrication protocol. A cross-section of membrane PES-1 is shown in FIG. 17. This shows that the morphology of the macrovoids of the polyethersulphone membrane was different to those of the polysulphone membranes. As the spinning solution formulations and fabrication protocol were, except for the composition of the external coagulation bath, identical for both membranes, the difference in morphologies could possibly be ascribed in the different coagulation pathways and glass-transition points that exist for the two polymer systems. Initial results also indicated that many of the macrovoids in the polyethersulphone membrane were dead-ended, and therefore not nearly as regular as those of membrane PSf-5.

Conclusions

It has thus been shown that an internally skinned membrane with narrow-bore macrovoids extending substantially the full width of the membrane and with no external skin layer can consistently be produced from at least polysulphone and polyethersulphone. The membranes have good mechanical strength and unique morphological properties, which make them useful for biotechnological and filtration separation applications.

The membrane formation process of the present invention may also be used to produce a membrane from polymers that have been modified to incorporate ligands onto which enzymes may covalently be bonded. A typical example is polyacrylonitrile-co-maleic anhydride or polymer materials that will result in membranes with fixed surface charges.

TABLE 1

Spinning solution formulations to produce membranes with finger-like macrovoids in substructure

| Component | Membrane code | | | |
| --- | --- | --- | --- | --- |
| | PSf-1 | PSf-2 | PSf-3 | PSf-4 |
| | Mass percent | | | |
| Ultrason S (PSf) | 26 | 24 | 24 | 24 |
| High boiling point solvent (NMP) | 51 | 46 | 56 | 36 |
| Low boiling point non-solvent additive (MC) | 2 | 10 | 10 | 10 |
| Low molecular mass polymer additive (PEG600) | 11 | 10 | | 30 |
| High molecular mass polymer additive (PVP) | 10 | 10 | 10 | |

All the spinning solutions have unlimited shelf-life if the starting materials are dry

TABLE 2

Modified spinning solution formulations to enhance porosity

| Component | Membrane code | |
| --- | --- | --- |
| | PSf-5 | PES-1 |
| | Mass percent | |
| Ultrason S (PSf) | 22 | |
| Ultrason E (PES) | | 22 |
| High boiling point solvent (NMP) | 36 | 36 |
| Low boiling point non-solvent additive (MC) | 10 | 10 |
| Low molecular mass polymer additive (PVP) | 32 | 32 |

TABLE 3

Water content of aqueous solvent external coagulation bath

| Membrane code | Water content |
| --- | --- |
| | Mass percent |
| PSf-5/1 | 4,3 |
| PSf-5/2 | 6,1 |
| PSf-5/3 | 7,9 |

Water content determined by Karl Fischer titration

What is claimed is:

1. A method of making a hollow fibre membrane comprising extruding a membrane-forming polymer solution through the annulus of a tube-in-orifice spinneret to form a nascent hollow membrane, there being a lumen coagulant in the lumen of the nascent membrane being contacted with an external coagulant having a solvent content which is such that, at the interface between the nascent membrane and the external coagulant, liquid—liquid phase separation rather than gelation is thermodynamically the favored process, and thereafter subjecting the outside of the nascent membrane to a vapour-phase, non-solvent environment to induce precipitation of the phase-separated polymer.

2. A method according to claim 1, wherein the external coagulant has a solvent content which is such that, in a phase diagram of the ternary system consisting of the solvent component of the coagulant, the non-solvent component of the coagulant, and the polymer, and having a solvent-non-solvent axis, a demixing gap, and a binodal curve at the boundary of the demixing gap, and composition of the external coagulant lies within 5% of the point where the binodal curve intersects the solvent-non-solvent axis.

3. A method according to claim 1, wherein the external coagulant has a solvent content which is such that, in a phase diagram of the ternary system consisting of the solvent component of the coagulant, the non-solvent component of the coagulant, and the polymer, and having a solvent-non-solvent axis, a demixing gap, and a binodal curve at the boundary of the demixing gap, the composition of the external coagulant lies outside the demixing gap.

4. A method according to claim 3, wherein the solvent content of the external coagulant is such that the composition thereof lies within 5% of the point where the binodal curve intersects the solvent-non-solvent axis.

5. A method according to claim 1, wherein the external coagulant is a solution of polymer solvent in water.

6. A method according to claim 5, wherein the water content of the external coagulant is less than 20% by volume.

7. A method according to claim 5, wherein the water content of the external coagulant is less than 9% by volume.

8. A method according to claim 7, wherein the water content of the external coagulant is about 2% by volume.

9. A method according to claim 1, wherein the vapour of the non-solvent vapour phase environment is water vapour.

10. A method according to claim 1, wherein the polymer of the membrane-forming polymer solution is polysulphone.

11. A method according to claims 1, wherein the polymer of the membrane-forming polymer solution is polyethersulphone.

12. A method according to claim 1, wherein the membrane-forming polymer incorporates ligands onto which enzymes are covalently bondable.

13. A method according to claim 12, wherein the membrane-forming polymer is polyacrylonitrile-co-maleic anhydride.

* * * * *

UNITED STATES PATENT AND TRADEMARK OFFICE
CERTIFICATE OF CORRECTION

PATENT NO. : 5,833,896

DATED : November 10, 1998

INVENTOR(S) : Edmund P. JACOBS et al.

It is certified that error appears in the above-indentified patent and that said Letters Patent is hereby corrected as shown below:

In claim 1, please replace "lumen of the nascent membrane" with --lumen of the nascent membrane, and the outside of the nascent membrane--;

In claim 2, please replace "and composition" with --the composition--;

In claim 11, please replace "claims 1" with --claim 1--.

Column 1, line 59, please replace "illustrate" with --illustrates--;

Column 6, line 9, please replace "through" with --thought--;

Column 7, line 1, please replace "1,2" with --2,1--.

Signed and Sealed this

Eleventh Day of January, 2000

Attest:

Q. TODD DICKINSON

Attesting Officer

Acting Commissioner of Patents and Trademarks